United States Patent [19]
Tschoegl

[11] 3,933,032
[45] Jan. 20, 1976

[54] DYNAMIC RHEOMETER

[75] Inventor: Nicholas W. Tschoegl, Pasadena, Calif.

[73] Assignee: California Institute of Technology, Pasadena, Calif.

[22] Filed: Sept. 1, 1971

[21] Appl. No.: 176,873

[52] U.S. Cl. .................. 73/67.1; 73/94; 73/100
[51] Int. Cl.² .................................... G01N 3/32
[58] Field of Search ............ 73/67, 67.1, 92, 93, 94, 73/100

[56] References Cited
UNITED STATES PATENTS

| | | | |
|---|---|---|---|
| 2,873,604 | 2/1959 | Samsel | 73/67.1 |
| 3,033,027 | 5/1962 | Perls et al. | 73/67.1 X |
| 3,162,039 | 12/1964 | Schloss | 73/67.1 |

OTHER PUBLICATIONS
"Direct Measurement of Dynamic Bulk Modulus," NBS Technical News Bulletin, pp. 110, 111, Aug. 1956.

Primary Examiner—James J. Gill
Attorney, Agent, or Firm—Lindenberg, Freilich, Wasserman, Rosen & Fernandez

[57] ABSTRACT

The dynamic mechanical properties of polymeric materials can be measured either in uniaxial compression or in flexure as a function of frequency over a wide frequency as well as temperature range, by using a piezoelectric driver to apply a displacement to a sample and a piezoelectric pickup to pick up the forces transmitted through the sample together with electrical circuitry whereby the amplitude ratio and phase angle between drive and pickup signals may be read.

9 Claims, 3 Drawing Figures

DYNAMIC RHEOMETER

FIELD OF THE INVENTION

This invention relates to apparatus used for measuring compression and/or flexure properties of materials and more particularly to improvements therein.

OBJECTS AND SUMMARY OF THE INVENTION

An object of this invention is to provide apparatus that can measure the dynamic mechanical properties of polymeric materials over a wide frequency and temperature range.

Another object of this invention is the provision of a novel and useful apparatus and system for measuring the dynamic mechanical properties of polymeric materials.

These and other objects of the invention are achieved in an arrangement wherein a displacement is applied to a specimen, whether in compression or in flexure, by means of a piezoelectric transducer comprising a stack of ceramic discs. The force resulting from the application of this displacement to the specimen are detected by a second piezoelectric transducer comprising a ceramic cylinder. The input and the output signals are processed by suitable phase and amplitude comparing circuitry and are then applied to a display device, such as a cathode ray tube, whereby the ratio of the amplitudes and the phase angle between the two signals may be readily seen and measured.

DESCRIPTION OF THE PREFERRED EMBODIMENT

Figure 1:
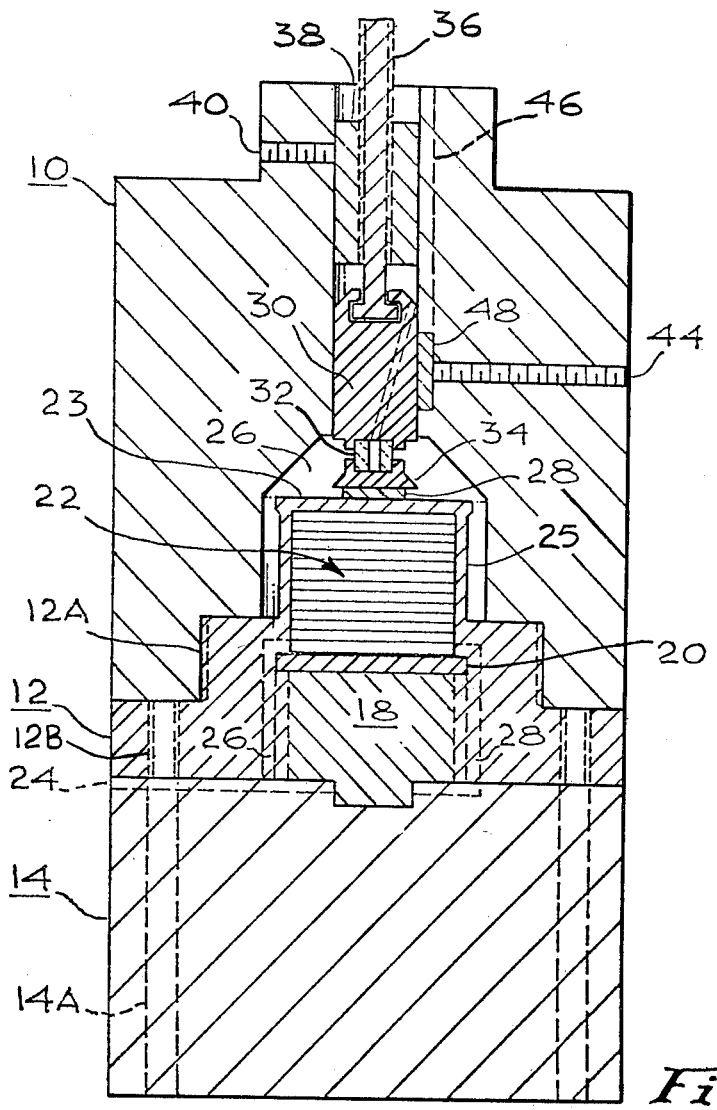
FIG. 1 is a cross sectional view of a dynamic rheometer in accordance with this invention.

Referring now to FIG. 1, there may be seen a cross sectional view of an embodiment of this invention comprising the dynamic rheometer for testing a specimen in compression. This includes an upper housing portion 10, having a cavity hollowed out of the center into which the pickup and driving equipment to be described will fit. A central housing portion 12 may be threaded, as by threads 12A, into the upper housing portion. A lower member 14, which essentially provides an inertial mass, is attached by bolts, not shown, which fit through bolt holes 14A, passing through the lower portion 14 into the threaded bolt holes 12B in the central housing portion 12.

Into a cavity in the central housing portion, there is threaded a pressure plug which is a solid block of metal 18. A keyed disc 20 is fitted on top of this block. The block is centrally located.

On the keyed disc 20 there is placed a stack of ceramic discs 22. This stack of discs constitutes the main element of the driving transducer for the invention. Electrical leads for applying a driving voltage to the discs may be brought to the discs through a slot 24, in the top of the lower member 14, and then through suitable slots 26, 28, as represented by the dotted lines on the drawing.

The ceramic discs are stacked so that adjacent faces of adjacent discs have a like polarity. Portions of the disc faces and sides may be coated with a conductive material so that connection may be made with the wires leading from a power supply. The technique for connecting wires to a stack of piezoelectric discs is well known and will not be described further here.

Integral with the intermediate housing section 12 is a thin walled cylindrical enclosure section. This enclosure section consists of a top plate 23 and thin side walls 25 acting as a restoring spring.

The stack of ceramic discs is placed into the enclosure section 23, 24, the keyed disc 20 is inserted and the pressure plug 18 is screwed to apply a desired pressure. Bolts are then used to bolt the lower member and the intermediate housing portion together.

The upper housing portion will include an opening 26 to afford access to the top plate 23 of the piezoelectric stack housing. In compression, the sample or specimen 28 is disc-shaped or cylindrical so that a sample or specimen 28 may be placed on the top plate 23. The piezoelectric stack fills the enclosure section 24 and the top disc abuts the underside of the top plate 23.

A cylindrical opening in the upper housing portion 10 permits sliding motion therein of a monitor support 30. The monitor support is a cylindrical piece of metal having a flat face on one side and having the pick up transducer 32 mounted at one end thereof. By way of illustration, the pick up transducer here is a piezoelectric cylinder 32, which is insulatingly attached to the monitor support 30, and its cylindrical axis aligned with the cylindrical axis of the monitor support 30. Between the piezoelectric pickup 32 and the sample 28, there is placed a monitor plate 34. The piezoelectric force pickup fits into a complementary circular opening in the monitor plate, and the opposite end of the monitor plate has a flat surface for engaging the sample to be tested.

The end of the monitor support opposite to the end at which the piezoelectric force pickup is mounted, has an opening therein large enough to receive and provide free rotation of the screw-like head of a micrometer screw 36. The micrometer screw is threaded through a micrometer barrel 38, which is inserted in the central opening in the upper housing portion. The position of the micrometer barrel may be fixed by means of a set screw 40, which is threaded through the upper housing. The micrometer screw is used to adjust the position of the piezoelectric force pickup as well as to apply an optional static pressure to the sample. When this adjustment has been made, a set screw 44 is turned to move a clamping shoe 48 against the flat face of the monitor support to clamp the monitor support 30 in position. The monitor support 30 has an opening drilled therethrough to communicate between the piezoelectric force pickup 32 and a slot 46, represented by dotted lines, whereby the leads to the piezoelectric force pickup may be brought out.

Figure 2:
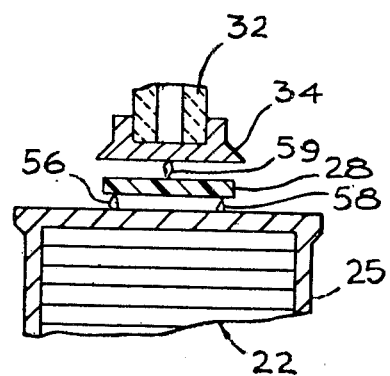
FIG. 2 is a cross sectional and fragmentary view illustrating an arrangement for testing a specimen in flexure in accordance with this invention.

FIG. 2 is a sectional view illustrating how this embodiment of the invention may be used for testing in flexure. Similar functioning parts will bear the same reference numerals as are shown in FIG. 1A. The top plate 23 of the piezoelectric stack housing 24 bears two knife edges 56, 58. These knife edges may always be in place, and are not shown in FIG. 1 to simplify the drawing. In compression the specimen is small enough to clear the knife edges. In flexure, a bar-shaped specimen is placed across these knife edges. The monitor assembly is moved until the knife edge 59 abuts the portion of the specimen 28B which is centrally located with respect to the portions contacted by the knife edges 56, 58.

Figure 3:
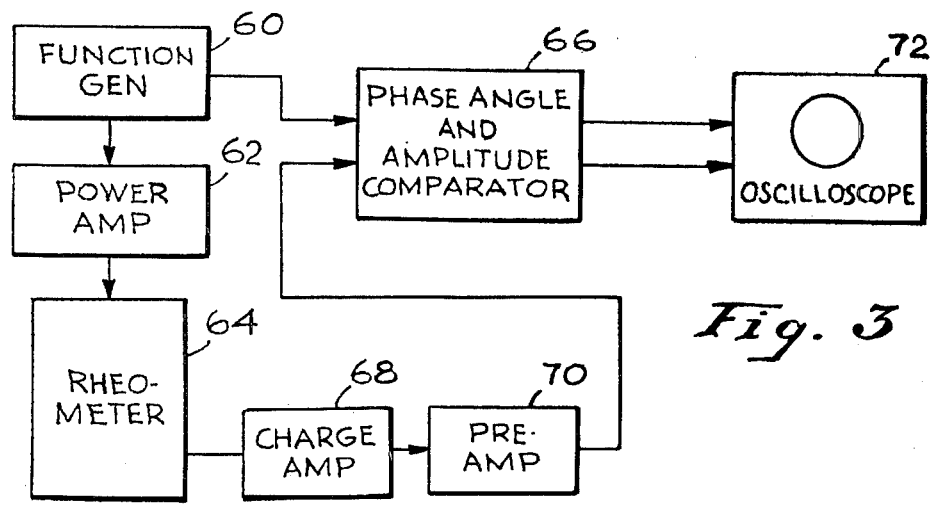
FIG. 3 is a block diagram, illustrating the electrical circuitry which may be employed with this invention.

FIG. 3 is a block diagram generally illustrative of the electrical components which may be employed with the embodiment of this invention. A function generator 60 provides oscillations having a desired wave shape and frequency for the kind of test desired. The output of the function generator is applied to a power amplifier 62, to be amplified for driving the piezoelectric stack 22 of the rheometer 64. The output of the function generator 60 is also applied to phase and amplitude comparator circuits 66.

The output voltage from the force pick up of the rheometer 64 is fed to a charge amplifier 68 and passes through a preamplifier 70 to the phase angle and amplitude comparator 66. The outputs of the phase angle and amplitude comparator consisting of the suitably processed signals are applied to some suitable measuring device such as, for example, a cathode ray oscilloscope 70. In this way, the phase angle and amplitude ratio between the two signals may be determined. Suitable methods for doing this are known in the art.

The apparatus shown herein may be calibrated by using stainless steel "Morehouse" rings of known elastance and negligible loss in place of a sample specimen.

The dynamic mechanical response functions, i.e. the storage modulus, $E'(\omega)$, loss modulus, $E''(\omega)$, storage compliance, $D'(\omega)$, loss compliance, $D''(\omega)$, and loss tangent, $E''(\omega)/E'(\omega) = D''(\omega)/D'(\omega)$ where $\omega$ is the radian frequency, are calculated from measurements of the amplitude ratio and phase angle.

The apparatus described hereinabove is able to measure the mechanical properties (Young's modulus) of polymeric materials either in uni axial compression or in flexure as a function of frequency from about 0.1 to 2000 Hz over a temperature range from $-100°$ to $+150°C$. The test specimen is subjected to extremely small deformations, an advantage which insures that measurements can be made within the linear range of most materials. Low modulus, (rubbery) materials are measured in compression. Typically, discs of 0.25 to 0.5 inch diameter, 0.1 to 0.2 inch high, are used as test specimens. High modulus materials (plastics) are measured in flexure. Strips typically 1 × 0.25 × 0.05 inch in dimensions are used as test specimens. The modulus range of the apparatus is very wide. Values as low as 50 psi and as high as 10 million psi are within its range.

Temperature control may be provided if desired by some suitable heating and cooling arrangement. The temperature in the cavity 26 and the central housing 12 may be measured by two thermocouples in a manner well known in the art.

From the foregoing, it will be seen that there has been described a novel, useful, and wide range capability test rheometer.

What is claimed is:

1. A dynamic rheometer comprising:
   a support base,
   a piezoelectric transducer means supported on said support base,
   means for supporting a specimen to be tested on said piezoelectric transducer means,
   a force pickup transducer,
   means for supporting said force pickup transducer on top of said specimen to be tested for generating signals responsive to motion of said specimen,
   power means for driving said piezoelectric transducer means for causing compression deflections and flexure deflections to said specimen, and
   means for comparing the phase and amplitude of the signals applied by said power means to said piezoelectric transducer means and the signals generated by said force pickup means in response to compression and deflection of said specimen.

2. A dynamic rheometer as recited in claim 1 wherein said piezoelectric transducer includes a stack of piezoelectric discs and said support base includes wall means for elastically enclosing the sides of said stack of piezoelectric discs.

3. A dynamic rheometer as recited in claim 1 wherein said piezoelectric transducer means is a stack of piezoelectric discs, and
   said force pickup transducer is a piezoelectric cylinder.

4. A dynamic rheometer as recited in claim 2 wherein there is included a top plate on said stack of piezoelectric discs having two upstanding wedge-shaped members for supporting a specimen for testing in flexure, and
   said force pickup transducer has a plate thereon with a wedge-shaped member positioned to contact said specimen midway between said two upstanding wedge-shaped members and on the side opposite to the one supported by said two wedge-shaped members.

5. A dynamic rheometer as recited in claim 1 wherein said means for supporting said force pickup transducer on said specimen to be tested includes a support block having said force pickup transducer attached to one end thereof, and
   micrometer means coupled to the other end of said support block for positioning said support block and said force pickup transducer means at a desired location.

6. A dynamic rheometer as recited in claim 5 wherein there is included housing means having an opening therein, wherein said piezoelectric transducer means, said specimen, said force pickup transducer means and said means for supporting said force pickup transducer means are supported, and
   means supported by said housing means for clamping said micrometer means at a desired location.

7. A system for measuring the dynamic mechanical properties of material in either compression or in flexure as a function of frequency comprising a dynamic rheometer including:
   a support base,
   a stack of piezoelectric discs mounted on said support base,
   means for supporting a specimen to be tested on said stack of piezoelectric discs,
   a cylindrical piezoelectric force pick up transducer,
   means for supporting said cylindrical piezoelectric force pick up transducer on said specimen to be tested, with its cylindrical axis normal to the plane established by said specimen to be tested,
   a source of signals having a desired frequency and amplitude,
   means for applying signals from said source to said stack of piezoelectric discs for applying flexure deflections and compression deflections to said specimen,
   means for measuring the phase angle and amplitude ratio between the signals applied to said stack of piezoelectric discs and signals generated by said cylindrical force pickup transducer responsive to deformations of said specimen, and means for applying signals from said source and from said cylindrical piezoelectric force pickup to said means for measuring.

8. A dynamic rheometer as recited in claim 7 wherein said support base includes wall means for elastically enclosing the sides of said stack of piezoelectric discs, said means for supporting a specimen to be tested on said stack of piezoelectric discs includes a plate on said elastic walled housing means on which said specimen is placed.

9. A dynamic rheometer as recited in claim 7 wherein said plate has a pair of spaced upstanding wedge-shaped members for supporting a specimen for testing in flexure, and said force pick up transducer has a plate thereon with a wedge-shaped member positioned to contact said specimen midway between said two upstanding wedge-shaped members on the side to the one supported by said two wedge-shaped members.

* * * * *